(12) United States Patent
Touchstone

(10) Patent No.: US 7,871,268 B2
(45) Date of Patent: Jan. 18, 2011

(54) METHOD AND APPARATUS FOR SELECTING NON-OPACIOUS DENTAL MATERIALS

(76) Inventor: C. Alex Touchstone, 108 S. 21st Ave., Hattiesburg, MS (US) 39401

( * ) Notice: Subject to any disclaimer, the term of this patent is extended or adjusted under 35 U.S.C. 154(b) by 194 days.

(21) Appl. No.: 11/872,491

(22) Filed: Oct. 15, 2007

(65) Prior Publication Data

US 2008/0090197 A1      Apr. 17, 2008

Related U.S. Application Data

(63) Continuation of application No. 11/159,795, filed on Jun. 23, 2005.

(60) Provisional application No. 60/642,167, filed on Jan. 6, 2005.

(51) Int. Cl.
*A61C 13/08* (2006.01)

(52) U.S. Cl. .................................. 433/203.1; 433/26

(58) Field of Classification Search ................ 433/26, 433/203.1, 215, 202.1
See application file for complete search history.

(56) References Cited

U.S. PATENT DOCUMENTS

| | | | | |
|---|---|---|---|---|
| 2,202,713 A | * | 5/1940 | Myerson | 433/208 |
| 4,828,117 A | * | 5/1989 | Panzera et al. | 206/63.5 |
| 5,114,340 A | * | 5/1992 | Hahn | 433/26 |
| 5,240,414 A | * | 8/1993 | Thompson | 433/26 |
| 5,308,243 A | * | 5/1994 | Emmons | 433/203.1 |
| 5,562,448 A | * | 10/1996 | Mushabac | 433/215 |
| 5,624,262 A | * | 4/1997 | Yarovesky et al. | 433/223 |
| 5,725,372 A | * | 3/1998 | Leon | 433/26 |
| 5,743,730 A | * | 4/1998 | Clester et al. | 433/26 |
| 5,759,030 A | * | 6/1998 | Jung et al. | 433/29 |
| 5,766,006 A | * | 6/1998 | Murljacic | 433/26 |
| 5,800,164 A | * | 9/1998 | Pfau | 433/26 |
| 6,030,209 A | * | 2/2000 | Panzera et al. | 433/26 |
| 6,033,222 A | | 3/2000 | Schneider, II et al. | |

(Continued)

FOREIGN PATENT DOCUMENTS

EP      1252867      10/2002

(Continued)

OTHER PUBLICATIONS

International Publication No. WO 2004/0098378 A2, published Nov. 18, 2004, to Orametrix, Inc.

(Continued)

*Primary Examiner*—Cris L Rodriguez
*Assistant Examiner*—Hao D Mai
(74) *Attorney, Agent, or Firm*—Waddey & Patterson; Gary L. Montle; Edward D. Lanquist, Jr.

(57) ABSTRACT

A method and system for selecting dental constructions using translucent materials that match an individual's preexisting tooth appearance uses a set of reference templates. The reference templates are constructed from layers of various translucent dental materials positioned on bases constructed from actual or simulated tooth structures. The layers of translucent materials have a thickness that varies in increments that correspond to the likely thicknesses of the materials when used in dental constructions. A reference table is created based upon color measurements of each of the reference templates. A color measurement of the individual's preexisting teeth is then compared to the reference table to determine which particular dental construction will most closely match the individuals preexisting teeth.

8 Claims, 1 Drawing Sheet

U.S. PATENT DOCUMENTS

| | | | | |
|---|---|---|---|---|
| 6,250,926 | B1* | 6/2001 | Foser et al. | 433/218 |
| 6,254,385 | B1* | 7/2001 | Jung et al. | 433/26 |
| 6,328,567 | B1 | 12/2001 | Morris et al. | 433/215 |
| 6,358,047 | B2* | 3/2002 | Lehmann | 433/26 |
| 6,499,998 | B2* | 12/2002 | Kerschbaumer et al. | 433/26 |
| 6,568,936 | B2 | 5/2003 | MacDougald et al. | |
| 6,743,014 | B2* | 6/2004 | Kerschbaumer et al. | 433/26 |
| 6,755,646 | B2* | 6/2004 | Zun | 433/26 |
| 6,925,205 | B2* | 8/2005 | Leedham et al. | 382/167 |
| 6,951,459 | B2* | 10/2005 | Weinstein | 433/26 |
| 7,086,863 | B2* | 8/2006 | Van der Zel | 433/223 |
| 7,153,135 | B1* | 12/2006 | Thomas | 433/213 |
| 2001/0049082 | A1* | 12/2001 | Kerschbaumer et al. | 433/26 |
| 2002/0048400 | A1* | 4/2002 | Leedham et al. | 382/167 |
| 2002/0081547 | A1 | 6/2002 | Kerschbaumer et al. | |
| 2003/0124481 | A1* | 7/2003 | Zun | 433/26 |
| 2003/0180687 | A1* | 9/2003 | Mrotzek et al. | 433/202.1 |
| 2004/0067465 | A1 | 4/2004 | Schomann | |
| 2008/0090197 | A1 | 4/2008 | Touchstone | |

OTHER PUBLICATIONS

International Publication No. 2005/072227 A2, published Aug. 11, 2005, to Gerber Scientific Products, Inc.

International Publication No. WO 2006/031096 A1, published Mar. 23, 2006, to Oratio B.V.

European Patent Office Search Report dated May 15, 2008 for PCT/US2006000453.

\* cited by examiner

METHOD AND APPARATUS FOR SELECTING NON-OPACIOUS DENTAL MATERIALS

CROSS-REFERENCES TO RELATED APPLICATIONS

This application claims benefit of each of the following noted applications, and the relationship of this application to each prior application is noted below:
(1) this application is a continuation of co-pending U.S. patent application Ser. No. 11/159,795 ("the '795 application"), filed Jun. 23, 2005, entitled "Method and Apparatus For Selecting Non-Opacious Dental Materials";
(2) the '795 application claims the benefit of co-pending provisional U.S. Patent Application Ser. No. 60/642,167, filed Jan. 6, 2005, entitled "Method and Apparatus for Determining the Dental Material(s) that Will Result in the Correct Final Color of a Non-Opacious Dental Restoration by Measuring and Predicting the Influence of the Color Of Prepared Teeth on the Final Color" which is hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

FIELD OF THE INVENTION

The present invention is generally directed toward the field of dental reconstructions. More particularly, the present invention is directed toward a method and apparatus for the selection of a dental restoration that uses a non-opacious material such that the final dental restoration will match the color and appearance of an individual's teeth.

BACKGROUND OF THE INVENTION

The present invention relates to a shade or color determination apparatus and method for dental restorations where translucent materials are used that account for the influence of underlying tooth structure on the final shade of the dental restorations when an opaque layer of dental material is not used in the fabrication of the dental restoration.

A shade determination apparatus and method is known from U.S. Pat. No. 6,499,998 which discloses a method for specifying and determining appropriate colors for teeth and dental restorations in accordance with a set of reference templates. A shade guide such as disclosed in the '998 patent has a plurality of color groups, wherein each group is representative of a tooth with a certain brightness, saturation and/or hue and, thus, is assigned a certain shade. Each individual shade in a shade guide is termed a shade tab and is typically fabricated to resemble the shape of an upper incisor tooth with a material structure of one to as many as five or more layers of material.

A shade guide is limited in its effectiveness as a shade determination device. First, commercial shade guides have a limited number of shade tabs. Moreover, the user's ability to discern one shade from another is often compromised by the user's inability to discern small color differences due to eye strain, non-standard lighting conditions or by problems with the user's anatomy related to color discrimination.

Additional problems arise in achieving an accurate shade match using a commercial shade guide due to differences in the physical and, thus, light refractive properties of the materials used to manufacture the shade guides themselves versus the materials used to fabricate dental restorations.

While systems similar to that described in the aforementioned U.S. Pat. No. 6,499,998 aim to overcome many of the limitations inherent in the use of commercial shade guides, they fail to address the influence of the color of the underlying tooth structure on the final shade of a dental restoration when translucent dental materials are used without an opaque layer to mask out the internal structure's influence.

Until recently, the use of an opaque layer in the fabrication of dental restorations was the norm. However, with the introduction and increasing use of more durable translucent dental ceramics in the fabrication of dental restorations, an opaque core material is often no longer employed. Because these ceramic restorations have no opaque core, the final color of the restoration is influenced by the color, or shade, of the prepped tooth that underlies and supports the restoration itself. However, the prior art, including U.S. Pat. No. 6,499,998, fails to take into account the significant influence of the underlying tooth structure. The present application addresses this key issue in a novel and commercially viable manner.

BRIEF SUMMARY OF THE INVENTION

An object of the present invention is therefore to provide a dental material(s) and/or shade selection apparatus that will measure, predict and accurately account for the influence of the underlying prepared tooth on the final shade of a dental restoration when layer(s) of translucent dental materials are used without an opaque masking layer thereby significantly improving shade matching in such circumstances.

This object is achieved in accordance with the apparatus and method of the present invention. In particular, the apparatus contains coloration data derived from a set of reference templates for comparison to a patient's tooth which are fabricated from the dental materials to be used in actual dental restorations as well as coloration data derived from simulated and/or actual tooth structures. The dental materials templates are manufactured using the same method(s) as those which are used in the fabrication of the dental restorations themselves, taking into account layer thickness, layer arrangement, and/or material selection that correspond to the dental restoration, filling, or tooth that is to be employed. The simulated tooth structure templates are manufactured from materials that have physical properties that approximate that of natural tooth structure, e.g. enamel and/or dentin. The actual tooth structure templates are derived from extracted and preserved human and/or bovine and/or other animal teeth. The apparatus also has a storage apparatus that contains the coloration measurements of the reference templates, both measured individually and in various layered arrangements which represent the combinations of materials to be employed in dental restorations. The coloration data of individual templates and layered templates are measured and stored both alone and in combination with underlying layer(s) of simulated and/or natural tooth structure. The apparatus also stores the coloration measurements of templates of simulated and/or natural tooth structures individually. Measurements of the colorations of the aforementioned individual and/or layered templates are made using a known instrumental color determination device such as a spectrophotometer or colorimeter.

The resultant coloration values and relevant layering order and template thickness information are entered into the apparatus and stored for later comparison. In order to make an appropriate material selection, the average thickness of the presentation surface of the planned dental restoration is determined from a known outside source and entered into the apparatus. Additionally, the desired final shade of the restoration as well as the prepared tooth shade are determined by any preferred known method or by the instrumental color determination device used to measure the template(s) and tooth structure and entered into the apparatus. A mathematical comparison of the desired final restoration coloration data is made to that of the coloration data of the template(s) that contain an underlying layer of either simulated or natural tooth structure that corresponds to the coloration data for the prepared tooth. The template combinations that are compared are not limited to those who have the same composite thickness as the planned dental restoration. Based on these calculations, the apparatus proposes the material combination that results in the closest color match possible given the data previously entered. The apparatus also reports the degree to which each proposed combination differs from the desired final color of the restoration. The apparatus also proposes solutions for improved matching, taking into account changes in material thickness or alteration of prepared tooth color or the application of color modifiers to either the internal or external surface of the dental restoration either during or subsequent to the manufacturing process.

An embodiment of the present invention is directed toward a structure for use in selecting a translucent dental restoration that will match an individual's existing tooth appearance. The structure includes a plurality of reference templates for comparison to a desired tooth appearance. The plurality of reference templates are representative of a range of colors of enamel and/or tooth structures found in nature. Each template includes a base tooth structure constructed of an actual or simulated tooth structure covered with at least one layer of a translucent dental material. The layer of translucent dental material preferably comprises a circular wafer of dental material having a known thickness that is representative of the desired dental restoration thickness and a diameter that is in the range of approximately 12 mm. (The actual or simulated tooth structure preferably comprises a natural tooth structure encased in a fixation medium or a synthetically grown cellular material.) In an alternative embodiment, the layer of translucent dental material includes a second layer of translucent dental material for positioning over the first layer of translucent dental material to simulate a multilayered dental composition and the base tooth structure comprises at least two layers of simulated or actual tooth structures. The reference templates include a plurality of templates having a layer of the same translucent dental material wherein each template has a thicknesses ranging from a minimum thickness to a maximum thickness in a predetermined number of increments. The plurality of templates also preferably have layers of translucent dental material made from a plurality of different colored dental materials wherein a plurality of templates having a thickness ranging from a minimum thickness to a maximum thickness in predetermined increments is provided for each color of the translucent dental material. The templates are compared to a desired tooth appearance to determine the proper restoration for a given procedure.

Yet another embodiment of the present invention is directed toward a method of determining a dental restoration for use in a dental procedure related to at least one tooth of an individual that matches a pre-existing appearance of the individual's tooth. In accordance with the method, a series of reference templates are constructed wherein each template includes at least one simulated or actual tooth structure covered with at least one layer of a translucent dental material. The reference templates are evaluated in accordance with a color measurement method to produce a color value associated with each of the reference templates. The results of the evaluation are cataloged and stored in a computer database to create a reference database. The individual's pre-existing tooth appearance is evaluated in accordance with the color measurement method to produce a color value associated with the individual's pre-existing tooth appearance. A dental restoration associated with a reference template that has a color value that corresponds to the color value associated with the individual's tooth is selected for use in performing the dental procedure for the individual. In an especially preferred embodiment, the selection of the dental restoration is performed automatically by a computer based upon the reference database and the color value associated with the individual's tooth. The selection is also based upon an expected thickness of the dental construction provided to the computer by a user. Alternatively, the approximate thickness of the dental construction may be determined by a dental restoration CAD/CAM program.

A desired final tooth shade and a prepared tooth shade may be manually provided to the computer by a user. The computer then performs color difference calculations to determine a dental restoration that results in a smallest color difference between the preexisting tooth's appearance and the dental restoration.

Yet another embodiment of the present invention is directed toward a device for determining a dental restoration to be used in a dental procedure such that the dental restoration will have an appearance that substantially matches a pre-existing tooth appearance. The device includes a memory for storing a database containing a plurality of experimentally determined color values wherein each color value is associated with a dental restoration having at least one actual or simulated tooth structure and at least one translucent layer of dental material. A user input device allows a user to enter parameters concerning the dental procedure. A color measurement apparatus is used to determine a coloration measurement value for the individual's preexisting, prepared or reduced tooth appearance. A processor automatically selects a dental material(s) for use in the dental procedure based upon the user entered parameters and the database of experimentally determined color values. Preferably, the user enters an expected thickness of the dental construction and the processor uses the thickness in selecting the dental restoration. Alternatively, a dental CAD/CAM program can be used to automatically determine an expected thickness of a dental restoration for use in the dental procedure.

The inventive measures described herein make it possible for the first time to accurately select translucent dental materials that will result in adequate final coloration of the dental restoration even though no opaque masking layer is employed. This is based particularly on the fact that reference templates are used that correspond to the materials used, the underlying tooth structures and to the order in which they are layered and to the thickness of each layer as well as the average thickness of the restoration to be fabricated. The comparison apparatus and method result in more precise, consistent color matching of the final dental restoration to that of the desired color than in any previous method that uses translucent dental materials that do not include an opaque masking layer.

In accordance with the invention, it is advantageous to select simulated and/or natural tooth templates that include colors that correspond to the colors of teeth found in nature and to known dental color systems. Therefore, the simulated or actual tooth templates are created in a plurality of colors that correspond to the same. Likewise, it is particularly advantageous for the dental material templates to correspond in thickness and/or layering order to the thicknesses and layering orders that are commonly employed in the fabrication of dental restorations. The dental material templates will therefore be created in varying thicknesses and combined with one another in varying combinations that correspond to those commonly employed in practice.

In accordance with the invention, it is also advantageous to arrive at the appropriate materials to be used through an automated process. The relevant data is therefore displayed on a commonly available computer screen along with patient data information. The data may be converted to a printed format. In accordance with the invention, it is particularly advantageous for the data generated to be presented on the screen in one or more formats, including but not limited to numerical values, mapping of the coloration of the planned dental restoration overlaid on an outline of a tooth, alternate materials selections and their impact on the color match, user selectable color matching tolerance ranges and warnings when the tolerance ranges have been exceeded.

In accordance with the invention, it is advantageous for a variety of custom color matching algorithms to be user selectable, giving the user the option to increase or decrease the weight of individual parameters in the determination of an acceptable color match. The relative weight of parameters of material thickness, region of the tooth considered, material type(s), material layering order, variation of the overall or regional color of the prepped tooth, and predicted final dental restoration color, as well as any other parameter that is a part of the color matching formula employed, are all user adjustable. Thus, the present invention allows the user to custom tailor the functionality of the device to suit individual color matching needs.

BRIEF DESCRIPTION OF THE SEVERAL VIEWS OF THE DRAWINGS

Additional advantages, features and details of the invention result from the following description of exemplary embodiments with the aid of the accompanying drawings, in which.

DETAILED DESCRIPTION OF THE INVENTION

The present invention is directed toward an apparatus and method for measuring the influence of prepared or reduced teeth, also referred to herein as underlying tooth structure, on the final shade of a dental restoration when translucent dental materials are used without an opaque layer. In accordance with the invention, a set of reference templates are layered over simulated or actual teeth, whereby instrumental measurements of the coloration of sandwiches of teeth and templates can be determined. The templates and teeth are arranged in a layered arrangement that corresponds to the order in which they are found in commonly used dental restorations, taking into account layer thickness, materials used and preparation and/or manufacturing methods commonly employed. The colorations of the actual or simulated teeth and the colorations of the templates are measured separately.

The coloration data of both the layered sandwiches of templates and simulated or actual teeth and of the simulated or actual teeth themselves and of the templates themselves are stored in a storage apparatus for comparison purposes. The influence of the simulated or actual tooth on a given material combination is determined by mathematical comparison of the coloration of the simulated or actual teeth alone versus the combination of material layer(s) and the simulated or actual teeth. Likewise, the desired coloration or final shade is entered into the storage apparatus and the combination(s) of materials that result in the desired final shade are proposed based on mathematical comparisons.

Figure 1:
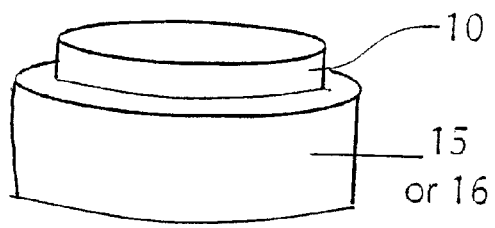
FIG. 1 is a perspective side elevation of the first combination of layered reference templates.
Figure 6:
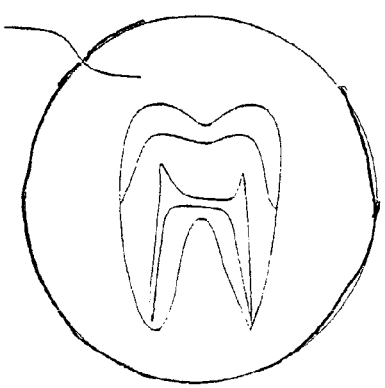
FIG. 6 is a plan view of the template of a cross section of natural tooth structure embedded in a fixation medium.

Referring now to FIG. 1, an exemplary illustration of an embodiment of a plurality of similar reference templates comprised of a plurality of material layers including at least one translucent dental material layer and at least one underlying layer of simulated or actual tooth structure is shown. The combination reference template illustrated in this exemplary embodiment represents a monochromatic dental restoration that does not contain an opaque layer. Material layer 10 is preferably formed as a circular wafer of dental material at a certain known thickness and diameter. The method used to form the material is one of many common to the industry and corresponds to the methods that are to be employed in the fabrication of the actual dental restorations to be used. Material layer 15 is formed from either simulated or natural tooth structure. In the case of layers formed of natural tooth structure, the tooth specimen is either encased in a fixation medium and sectioned as illustrated in FIG. 6, or is formed from natural cellular material through a synthetic growth method, the details of which are outside the scope of the present invention. Although this exemplary embodiment illustrates circular layers, any shape that is conducive to the color measurement procedures may be employed. To better illustrate the layers of the reference template and their corresponding order, the wafer thicknesses shown in the figures are not necessarily drawn to scale.

A plurality of circular wafers 12 mm in diameter of the same dental material and the same color are manufactured at thicknesses ranging from 0.2 mm to 2.0 mm in 0.1 mm increments. The diameter of 12 mm is generally preferable although not an absolute requirement. Adjustments in this dimension may be made to accommodate for the particular requirements related to the sample size accepted by the measurement instrumentation used. Similarly, a plurality of wafers made from each color of each dental material to be considered for use in the dental procedures are manufactured at thicknesses ranging from 0.2 mm to 2.0 mm in 0.1 mm increments.

Figure 5:
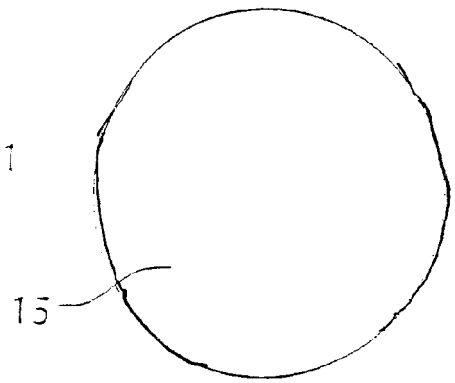
FIG. 5 is a plan view of the template of simulated tooth structure or of synthetically-grown natural tooth structure.

A plurality of wafers of material that simulate the optical characteristics of natural tooth structures is manufactured using known methods the details of which are outside the scope of this invention. The plurality of created wafers is representative of the range of colors of enamel and/or dentinal tooth structures found in nature. At a minimum, reference wafers are produced in different colorations which match the colors of the 24 colorations most commonly found in nature. These wafers are preferably 18 mm in diameter and 15 mm thick or, at a minimum, a thickness and diameter which are in excess of that required by the color measurement instrumentation to minimize edge loss or light scattering errors. However, it will be readily appreciated by those skilled in the art that adjustments in the diameter of the wafers may be made to accommodate for the particular requirements related to sample size accepted by the measurement instrumentation used. FIG. 5 illustrates an exemplary embodiment of a wafer 15 of simulated or synthetically-grown natural tooth structure.

Alternately, a plurality of wafers of natural tooth structure may be fabricated by embedding actual human, bovine or other animal teeth in a fixative medium and sectioned at a location that is representative of the area of the tooth that is to be used for reference measurements. The thickness of the sectioned wafers is preferably 15 mm or, at a minimum, in excess of that required by the color measurement instrumentation to minimize edge loss or light scattering errors. The diameter of the plurality of sectioned tooth structure wafers is 18 mm. As set forth above, adjustments in this dimension may be made to accommodate for the particular requirements related to sample size accepted by the measurement instrumentation used. A plurality of wafers of the natural tooth structures are created that are representative of the range of colors of enamel and/or dentinal tooth structure found in nature. At a minimum, reference wafers are produced in different colorations which match the colors of the 24 colorations most commonly found in nature. FIG. 6 illustrates an exemplary embodiment of a wafer 16 constructed from a natural tooth structure.

The assembled reference template illustrated in FIG. 1 includes one monochromatic dental material, wafer 10, centered over and adjacent to either simulated or actual tooth structure, illustrated as either wafer 15 or 16. The two layers are coupled to one another in a temporary fashion by means of a liquid, optically-transparent coupling medium. The aforementioned method of temporary coupling allows for a plurality of combinations of materials and tooth structures to be created and measured without the need for any unnecessary duplication of wafer samples.

Figure 2:
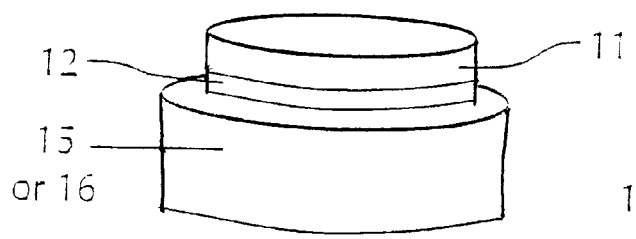
FIG. 2 is a perspective side elevation of the second combination of layered reference templates.

FIG. 2 illustrates an exemplary embodiment of a modified reference template wherein two layers, wafers 11 and 12 of dental restorative material and one layer, 15 or 16, of simulated or actual tooth structure are employed. In this instance, wafer 11 is a simple enamel layer of the planned dental restoration and layer 12 is the dentinal layer. The combination reference template that is formed in this exemplary embodiment represents a simple polychromatic dental restoration that does not contain an opaque layer. The enamel and dentinal reference wafers are manufactured in a manner which is generally known and corresponds to the methods to be used in the actual fabrication of dental restorations. A plurality of circular wafers 12 mm in diameter of the same dental material and the same color are manufactured at thicknesses ranging from 0.2 mm to 2.0 mm in 0.1 mm increments. The diameter of 12 mm is generally preferable although not a requirement. Adjustments in this dimension may be made to accommodate for the particular requirements related to sample size accepted by the measurement instrumentation used. Similarly, a plurality of wafers made from each color of each dental material to be considered are manufactured at thicknesses ranging from 0.2 mm to 2.0 mm in 0.1 mm increments.

In the exemplary embodiment illustrated in FIG. 2, the assembled reference template illustrated includes a dentinal dental material, wafer 12, centered over and adjacent to either simulated or actual tooth structure, illustrated as either wafer 15 or 16. The two layers are coupled to one another in a temporary fashion by means of a liquid, optically-transparent coupling medium. Next, a wafer of enamel dental material, wafer 11, is placed adjacent to and centered over the dentinal dental material, wafer 12 and coupled by means of the coupling medium. The combination reference template that is formed in the exemplary embodiment in FIG. 2 represents a two-layer, polychromatic dental restoration that does not contain an opaque layer.

Figure 3:
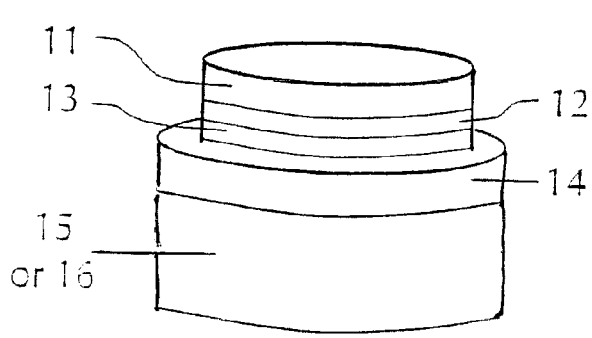
FIG. 3 is a perspective side elevation of the third combination of layered reference templates.

FIG. 3 illustrates an exemplary embodiment of a modified reference template wherein three layers, wafers 11, 12, and 13 of dental restorative material and two layers, wafer 14 and wafer 15 or 16, of simulated or natural tooth structure are combined to form the reference template. In the exemplary embodiment illustrated in FIG. 3, each dental restorative material wafer corresponds to a plurality of materials that are commonly used in the fabrication of dental restorations. For example, wafer 11 may be a simple enamel layer of the planned dental restoration, layer 12 the dentinal layer and layer 13 the deep dentinal or color modifying layer. The remaining two layers, wafer 14 and wafer 15 or 16 are both made in the aforementioned manner from either actual or simulated tooth structure. In the exemplary embodiment illustrated in FIG. 3, wafer 14 is made of either natural or synthetic enamel tooth material and wafer 15 or 16 is either natural or synthetic dentinal tooth material.

The combined reference template illustrated in FIG. 3 is constructed as in the aforementioned exemplary embodiments illustrated in FIG. 1 and FIG. 2 by arranging each layer in the order illustrated and coupling the layers to one another with an optically transparent liquid coupling medium. The combination reference template that is formed represents a more complex polychromatic dental restoration that does not contain an opaque layer. The thickness of each dental material layer corresponds to one of a plurality of thicknesses that are commonly employed in the layering of dental restorations, ranging from 0.2 mm to 2.0 mm. As in the other two embodiments, the diameter of the dental material wafers is generally selected to be 12 mm or a width that is conducive to measurement using commonly available instruments. Additionally, as in the other two previously discussed exemplary embodiments, a plurality of templates are constructed that contain a plurality of wafers of different thicknesses and colors representative of the various combinations that are commonly employed in the construction of actual dental restorations.

While the exemplary embodiments that are described herein are representative of the common order and level of layering complexity of dental restorations, it is obvious that the number of dental material wafer layers may be increased further to represent any arrangement of dental materials that may be employed either now or in the future and that the individual thicknesses and physical properties of the materials may also be varied according to current or future known manufacturing methods.

Figure 4:
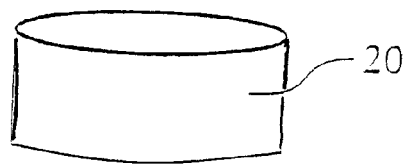
FIG. 4 is a perspective side elevation of a single layer of template material.

FIG. 4 illustrates an exemplary embodiment of a wafer, 20, of dental restorative material that is sufficiently thick in and of itself to facilitate accurate color analysis without induction of edge loss errors. The thickness of each material will vary according to that material's relative translucency in order to meet the aforementioned requirement. The wafers are analyzed using a known color measurement method such as a spectrophotometer or calorimeter.

It is obvious that the instrument used for analysis is preferably the same as that to be employed in the color measurement in the planning of the restoration of the patient's teeth. When this is not practical, the coloration of the patient's teeth can be determined by another means and input separately into the device for comparison and material matching purposes.

A measurement of the coloration of each material is made using a known color measurement instrument selected for generating the reference data. The data is stored in a computer database for analysis and comparison to other data collected as described herein. Next, the wafers 15 or 16 of synthetic or natural tooth structure are analyzed for their individual colorations using the same instrumentation. The coloration data generated are cataloged and stored in the computer database. Likewise, the various combined layers of wafers 14 and 15 or 16 are measured with the same instrumentation and the data is stored for later use. Data generated from the color measurements are stored in the storage apparatus along with the template layering order, wafer thickness(s) and other pertinent data.

The coloration of the combined reference templates illustrated as exemplary embodiments in FIG. 1, FIG. 2 and FIG. 3 is preferably analyzed with the same color measurement instrument as the individual's existing teeth such that variations due to the use of different equipment is minimized. The coloration data along with layering order, wafer thickness(s) and other pertinent cataloging information are stored in the storage apparatus. All logical combinations of layering of wafers of dental materials along with the coloration of synthetic or natural tooth structure are measured and the data recorded and assigned to its corresponding combined reference template.

All relevant combinations of materials are measured, totaling 1000 or more depending on the variety of materials considered for matching purposes. While it is obvious that the initial template preparation and data collection is somewhat laborious, the process has great advantage in that the data are collected one time and can then be used for any number of shade matching events as long as the same or optically similar dental materials are used in the actual fabrication of the planned dental restorations.

Once the coloration data has been gathered for all likely combinations of materials and tooth structure, the system is ready for use and can be made functional by one of several methods without deviating from the scope of the invention.

In one embodiment, the data are stored in a subprogram of an identical color measurement instrument to that which was used to gather the coloration data of the reference templates themselves. The end user, most commonly either a dentist or dental lab technician, simply uses the color measurement device to measure the coloration of the prepared tooth that is to be restored and the desired shade derived from measuring adjacent teeth. Alternatively, the desired shade of the planned dental restoration may be determined by the user by making a visual comparison using a commercially available shade guide and the desired shade of the restoration entered manually by the user. The user then manually enters the average thickness of the planned restoration. The thickness measurement can be made by one of several methods the details of which are outside the scope of the present invention. Then, the subprogram runs a series of color difference calculations and arrives at the best fit of dental materials which result in the smallest color difference between various materials combinations and the desired final shade, taking into account the measurement of the shade of the prepared tooth.

In a further embodiment, the data generated during the setup phase are stored in a stand-alone commercially available computer. In this case, the user manually enters the prepared tooth shade, the desired shade and the average thickness of the planned restoration. Using the data provided by the user, the computer performs color difference calculations to arrive at a proposal of materials that will result in the smallest color difference.

In a third embodiment, the reference template data generated are stored in a subprogram of a CAD/CAM dental restoration manufacturing unit. During the design phase of fabrication, the CAD/CAM machine automatically calculates the average thickness of the planned restoration and delivers the data to the subprogram; the user manually enters the desired final shade and the prepared tooth shade. The subprogram makes the appropriate color difference analyses and proposes the materials that will result in the closest shade match.

In a fourth embodiment, a color measurement instrument and the CAD/CAM dental restoration unit are linked to one another, either physically or wirelessly or by virtue of some other known communication method and the data generated are stored in a subprogram in either unit. The prepared tooth shade is measured with the color measurement device, the planned restoration average thickness is calculated by the CAD/CAM software, and the desired shade of the restoration is entered manually by the user or is determined by measurement of an adjacent tooth with the color measurement device. As in the other exemplary embodiments, the subprogram calculates the materials combination that results in the best shade match.

It is obvious that a number of other variations in the functionality of the method are possible without deviation from the scope of the invention. For instance, the program can be given a color difference tolerance range that will function to warn the user when this parameter is exceeded. Further, materials to be employed can be entered by the user and an estimate of the resultant shade of the restoration can be calculated. The program can also propose more than one combination of materials to arrive at the desired shade and present the color difference values for each combination, allowing the user to make the selection he or she deems appropriate.

In a further exemplary embodiment, the apparatus may take the form of a manual computing device such as a wheel wherein all but one variable is input and the solution to the remaining variable is read by the user.

It is also obvious that measurements of the color modifying layers of material can be included in the reference data. The color modifiers may take the form of surface stains or glazes on the dental materials themselves or that of layers of resin bonding agents that have physical properties such that they have an influence on the final coloration of the planned restoration. The data generated in these instances will then be used to provide additional material combinations and/or solutions to color matching problems.

The target area of the tooth for color matching may also be selected to suit the needs of the user. For instance, the middle one third of the labial surface of the tooth may be selected as the target area for anterior teeth whereas the occlusal surface might be considered preferable for posterior teeth. The average thickness and/or coloration measurements in the target area only will then be considered in the materials selection or color matching calculations.

The invention described herein addresses a heretofore unresolved problem of predicting the influence of prepared tooth structure on the final shade of dental restorations when an opaque layer of material is not used. It does so in a manner that is both useful and efficient.

Thus, although there have been described particular embodiments of the present invention of a new and useful Method and Apparatus for Determining the Dental Material(s) that Will Result in the Correct Final Color of a Non-Opacious Dental Restoration by Measuring and Predicting the Influence of the Color of Prepared Teeth on the Final Color, it is not intended that such references be construed as limitations upon the scope of this invention except as set forth in the following claims.

What is claimed is:

1. A device for determining one or more translucent dental materials used in a dental restoration so that covering the translucent dental materials over an individual's prepared tooth matches a desired tooth appearance, the device comprising:

a storage apparatus configured to store reference template parameters, the reference template parameters including a color value parameter associated with one of a plurality of reference templates having an actual or simulated tooth material covered by at least one translucent layer of dental material; and a computer system operatively linked to the storage apparatus, the system comprising an input device configured to receive input parameters related to the desired tooth appearance, a program configured to perform calculations utilizing the reference template parameters and the input parameters to select one or more translucent dental materials, the calculations dependent on a tooth shade of the prepared tooth and an influence of the tooth shade of the prepared tooth upon the desired tooth appearance, so that a difference between the desired tooth appearance and an appearance of the tooth after the restoration is minimized, and a processor for running the program.

2. The device of claim 1, the reference template parameters further including a reference template thickness parameter for each of the reference templates wherein the computer system utilizes the thickness parameter to select the translucent dental materials.

3. The device of claim 2, wherein the computer system further comprises a CAD/CAM program that automatically determines an expected thickness of the restoration for the prepared tooth so that the computer program can utilize the expected thickness to select the translucent dental material.

4. The device of claim 1, further comprising a color measurement apparatus that determines a coloration measurement value to measure the color value parameters.

5. The device of claim 1, wherein the input parameters further comprise the tooth shade of the prepared tooth.

6. The device of claim 5, wherein the input parameters further comprise a desired shade of the dental restoration.

7. The device of claim 6, wherein the input parameters further comprise an average thickness of the dental restoration.

8. The device of claim 1, wherein the program is configured to select one or more combinations of translucent dental materials, each combination calculated such that a difference between the desired tooth appearance and an appearance of the prepared tooth after the dental restoration is within a predetermined color tolerance range.

* * * * *